US010060892B2

(12) United States Patent
Watt et al.

(10) Patent No.: US 10,060,892 B2
(45) Date of Patent: Aug. 28, 2018

(54) TRIPODAL NITRATE RECEPTOR

(71) Applicant: University of Oregon, Eugene, OR (US)

(72) Inventors: Michelle Watt, Eugene, OR (US); Darren W. Johnson, Eugene, OR (US); Michael M. Haley, Eugene, OR (US)

(73) Assignee: University of Oregon, Eugene, OR (US)

(*) Notice: Subject to any disclaimer, the term of this patent is extended or adjusted under 35 U.S.C. 154(b) by 40 days.

(21) Appl. No.: 15/310,601

(22) PCT Filed: Dec. 11, 2014

(86) PCT No.: PCT/US2014/069717
§ 371 (c)(1),
(2) Date: Nov. 11, 2016

(87) PCT Pub. No.: WO2015/089271
PCT Pub. Date: Jun. 18, 2015

(65) Prior Publication Data
US 2017/0115262 A1    Apr. 27, 2017

Related U.S. Application Data (60) Provisional application No. 61/916,026, filed on Dec. 13, 2013.

(51) Int. Cl.
*G01N 31/00* (2006.01)
*G01N 31/22* (2006.01)
(Continued)

(52) U.S. Cl.
CPC ......... *G01N 31/227* (2013.01); *C07C 275/30* (2013.01); *C07C 275/34* (2013.01);
(Continued)

(58) Field of Classification Search
CPC .................................................. G01N 31/227
(Continued)

(56) References Cited

U.S. PATENT DOCUMENTS

2011/0015396 A1    1/2011   Haley et al.

FOREIGN PATENT DOCUMENTS

WO    WO 2015/089271 A1    6/2015

OTHER PUBLICATIONS

Masamichi Yamanaka, Tomoe Nakagawa, Ryohei Aoyama, Tomohiko Nakamura "Synthesis and estimation of gelation ability of C3-symmetry tris-urea compounds" Tetrahedron 64 (2008) 11558-11567 (Year: 2008).*
Jandke et al., Phenylquinoxaline Polymers and Low Molar Mass Glasses as Electron-Transport Materials in Organic Light-Emitting Diodes, (Macromolecules 1998, 31, 6434-6443) (Year: 1998).*
Watt et al., Selective Nitrate Binding in Competiitive Hydrogen Bonding Solvents: Do anion interactions facilitate nitrate selectivity?, vol. 52, pp. 10275-10280, dated Aug. 12, 2013 ,8 pages.
(Continued)

*Primary Examiner* — Christine T Mui
*Assistant Examiner* — Emily R. Berkeley
(74) *Attorney, Agent, or Firm* — Hickman Palermo Becker Bingham LLP (57) ABSTRACT

A compound, or a protonate or salt thereof, having a formula I of: wherein Y represents an optionally substituted aromatic group; n is 1 or 2; a is 0 to 4; $R^1$ and $R^2$ are each independently H; optionally substituted alkyl; optionally substituted aralkyl; acyl; phosphonyl; $-SO_2R^{12}$; $-C(O)R^{13}$; $-C(O)OR^{14}$; $-C(O)NR^{15}R^{16}$; $-C(O)CH_2R^{17}$; or $-C(S)-NR^{18}R^{19}$; $-S(O)R20$; or $-SO_2NR^{21}R^{22}$, wherein $R^{12}$-$R^{22}$ are each independently H, optionally substituted alkyl, optionally substituted aralkyl, optionally substituted aryl, or $-C(O)R^{23}$, wherein $R^{23}$ is H, optionally substituted alkyl, optionally substituted aralkyl, or optionally substituted aryl; and each $R^3$ is independently optionally substituted alkyl, halogen, optionally substituted alkoxy, optionally substituted carboxyl, amide; amino; or nitro.

16 Claims, 3 Drawing Sheets

(51) Int. Cl.
*C07C 275/30* (2006.01)
*C07C 275/34* (2006.01)
*C07C 335/18* (2006.01)
*C07C 275/42* (2006.01)
*C07C 335/16* (2006.01)
*C07D 251/24* (2006.01)

(52) U.S. Cl.
CPC .......... *C07C 275/42* (2013.01); *C07C 335/16* (2013.01); *C07C 335/18* (2013.01); *C07D 251/24* (2013.01); *G01N 31/22* (2013.01)

(58) Field of Classification Search
USPC ........................................................ 436/110
See application file for complete search history.

(56) References Cited

OTHER PUBLICATIONS

Sakai et al., InBr3-Promoted Divergent Approach (etc.), J. Org. Chem.,73 (11), pp. 4160-4165, pub. Apr. 29, 2008.
Korean Intellecutal Property Office, "International Search Report" in Application No. PCT/US2014/069717, dated Mar. 17, 2015, 4 pages.
Korean Claims in Application No. PCT/US2014/069717, dated Mar. 2015, 6 pages.
Adriaenssens et al., "Quantification of Nitrate Interactions and Selective Transport of Nitrate Using Calix (4) Pyrroles with Two Aromatic Walls", J. Am. Chem. Soc, vol. 135, pp. 8324-8330, May 14, 2013.

* cited by examiner

TRIPODAL NITRATE RECEPTOR

CROSS-REFERENCE TO RELATED APPLICATIONS

This application is a U.S. National phase of International Application No. PCT/US2014/06971, filed Dec. 11, 2014, which claims priority to U.S. Provisional Application No. 61/916,026, filed Dec. 13, 2013. The contents of both applications are incorporated herein by reference as if fully set forth herein.

ACKNOWLEDGMENT OF GOVERNMENT SUPPORT

This invention was made with government support under grant GM087398 awarded by the National Institutes of Health and grant DGE0742540 awarded by the National Science Foundation. The government has certain rights in the invention.

BACKGROUND

Anions are increasingly recognized as problematic environmental contaminants. For example, excess nitrate in soil from over-fertilization has led to contamination in water sources worldwide. Nitrate run-off into water sources causes algal blooms—a process known as eutrophication—ultimately depriving water of oxygen and leading to dead zones in the world's lakes and oceans. Given the negative impact nitrate has on water sources, there has been considerable interest in the design and synthesis of receptors capable of sensing the molecule in solution. A number of studies have reported synthetic neutral receptors capable of binding nitrate in solution; however, most exhibit low affinity. Some reports have shown enhanced nitrate binding in polar solvents such as $CHCl_3$ and even a few demonstrate high nitrate binding in more competitive solvents; however selectivity for nitrate remains rare.

SUMMARY

Disclosed herein are host or receptor compounds that bind targets of interest. In one embodiment the compounds bind ions. In particular, toxic ions, including anions and cations are bound by embodiments of the disclosed host compounds. In certain embodiments the receptor compounds bind nitrates.

Disclosed herein in one embodiment is a compound, or a protonate or salt thereof, having the formula I of:

wherein Y represents an optionally substituted aromatic group;
n is 1 or 2;
a is 0 to 4;
$R^1$ and $R^2$ are each independently H; optionally substituted alkyl; optionally substituted aralkyl; acyl; phosphonyl; $-SO_2R^{12}$; $-C(O)R^{13}$; $-C(O)OR^{14}$; $-C(O)NR^{15}R^{16}$; $-C(O)CH_2R^{17}$; or $-C(S)-NR^{18}R^{19}$; $-S(O)R^{20}$; or $-SO_2NR^{21}R^{22}$, wherein $R^{12}$-$R^{22}$ are each independently H, optionally substituted alkyl, optionally substituted aralkyl, optionally substituted aryl, or $-C(O)R^{23}$, wherein $R^{23}$ is H, optionally substituted alkyl, optionally substituted aralkyl, or optionally substituted aryl; and
each $R^3$ is independently optionally substituted alkyl, halogen, optionally substituted alkoxy, optionally substituted carboxyl, amide; amino; or nitro.

Further disclosed herein is a method for detecting for the presence of a target of interest in a system, comprising contacting a compound as disclosed herein with a sample from the system.

Exemplary compounds exhibit shifts and/or positive/negative responses in their spectral properties upon ligand binding. Accordingly, also disclosed are methods for using the host compounds to detect targets of interest, including neutral, cationic and anionic targets.

The foregoing will become more apparent from the following detailed description, which proceeds with reference to the accompanying figures.

DETAILED DESCRIPTION

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers group of the formula RC(O)— wherein R is an organic group.

The term "aliphatic" includes alkyl, alkenyl, alkynyl, halogenated alkyl and cycloalkyl groups. A "lower aliphatic" group is a branched or unbranched aliphatic group having from 1 to 10 carbon atoms.

The term "alkoxy" refers to a straight, branched or cyclic hydrocarbon configuration and combinations thereof, including from 1 to 20 carbon atoms, preferably from 1 to 10 carbon atoms, more preferably from 1 to 4 carbon atoms (referred to as a "lower alkoxy"), that includes an oxygen atom at the point of attachment. An example of an "alkoxy group" is represented by the formula —OR, where R can be an alkyl group, optionally substituted with, e.g., an alkenyl, alkynyl, aryl, aralkyl, cycloalkyl, halogenated alkyl, or heterocycloalkyl group as described herein. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers an aliphatic group that is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred lower alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl.

The term "amide" or "amido" is represented by the formula —C(O)NRR', where R and R' independently can be a hydrogen, alkyl, alkenyl, alkynyl, aryl, arylalkyl, cycloalkyl, halogenated alkyl, or heterocycloalkyl group described above. A suitable amido group is acetamido.

The term "amine" or "amino" refers to a group of the formula —NRR', where R and R' can be, independently, hydrogen or an alkyl (particularly lower alkyl), alkenyl, alkynyl, aryl, arylalkyl, carbonyl (e.g, —C(O)R", where R" can be hydrogen, an alkyl, alkenyl, alkynyl, aryl, or an arylalkyl), cycloalkyl, halogenated alkyl, or heterocycloalkyl group. For example, an "alkylamino" or "alkylated amino" refers to —NRR', wherein at least one of R or R' is an alkyl (particularly lower alkyl).

The term "aralkyl" refers to an alkyl group that is substituted with one or more aryl groups. A particular example of an aralkyl group is a benzyl group.

The term "aryl" refers to any carbon-based aromatic group including, but not limited to, phenyl, naphthyl, etc. The term "aromatic" also includes "heteroaryl groups," which are defined as aromatic groups that have at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carbonate" refers to a group of the formula —OC(O)O—. "Substituted carbonate" refers to a group of the formula —OC(O)OR. Likewise, as used herein the term "carbamate" refers to a group of the formula —OC(O)N(R)—, wherein R is H, or an aliphatic group, such as a lower alkyl group or an aralkyl group.

"Carboxyl" refers to a —COOH radical. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Optional" or "optionally" means that the subsequently described event or circumstance can but need not occur, and that the description includes instances where said event or circumstance occurs and instances where it does not. Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

The term "phosphoryl" refers to moieties of the formula —P(O)OR—, wherein R may be H, an aliphatic or aromatic moiety, a cation or a lone pair of electrons. Phosphoryl moieties may be further substituted to form phosphoramidates, phosphates and phosphonates.

The term "polyether moiety" may be an oligomer (which is inclusive of dimers and higher repeating units) or a polymer. Illustrative polyether moieties include those derived from an aliphatic polyether (e.g., paraformaldehyde, polyethylene glycol (PEG), polypropylene glycol, and polytetramethylene glycol, and those derived from an aromatic polyether (e.g., polyphenyl ether or poly(p-phenylene oxide)). A preferred polyether moiety is derived from PEG, also referred to herein as a poly(ethylene oxide). The PEG may be a straight chain PEG or a branched PEG. PEG is also inclusive of methoxypolyethylene glycol. In certain embodiments, the number of repeating ethylene oxide units in the PEG moiety may range from 2 to 50, more particularly from 2 to 10. The polyether moiety may be covalently bonded to the core motif via PEGylation procedures.

The term "sulfonyl" refers to the radical —$SO_2$—. The sulfonyl group can be further substituted with a variety of groups to form, for example, sulfonic acids, sulfonamides, sulfonate esters and sulfones.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

It is understood that substituents and substitution patterns of the compounds described herein can be selected by one of ordinary skill in the art to provide compounds that are chemically stable and that can be readily synthesized by techniques known in the art and further by the methods set forth in this disclosure.

The disclosed host compounds are useful, inter alia, as ion binding compounds. By way of example, specific anions bound by the disclosed compounds include, but are not limited to, toxic metal anions, halide anions, carboxylates, phosphates, sulfates, oxalates, terephthalates, phospholipids, nucleotides, oligonucleotides, DNA, RNA, anionic polyoxometalates, or oxoanions such as pertechnetate.

The structural formulas provided herein include salts of the illustrated compounds. Such salts can be formed when disclosed host compounds possess at least one basic group that can form acid-base salts with acids. Examples of basic groups present in exemplary disclosed host compounds include amino groups or imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Similarly, salts can be formed when disclosed host compounds possess at least one acidic group that can form acid-base salts with bases. Examples of acidic groups present in exemplary disclosed host compounds include carboxylic acid moieties and sulfonamide groups. Compounds that include at least one acidic group can form an acid-base salts with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. In addition, quaternary ammonium counterions also can be used.

Additionally, the structural formulas herein are intended to cover, where applicable, solvated as well as unsolvated forms of the compounds. "Solvate" refers to a compound physically associated with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compounds, methanol associated compounds, and the like. "Hydrate" is a solvate wherein the solvent molecule(s) is/are $H_2O$. Solvate complexes may be described in shorthand form for example as $(1.H_2O)_2$, which refers to a hydrate, more specifically a 2+2 complex of compound 1 with water.

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

Disclosed herein are new tripodal receptors that exhibit strong binding of nitrate in polar, competitive solvents, such as acetone, dimethyl sulfoxide and water. In certain embodiments, the receptors also show modest selectivity for nitrate over common interferents, such as chloride. Receptor 2 (shown below), lacking an electron-deficient aromatic ring, exhibits no such selectivity for nitrate. A close contact between nitrate and an alkyne within the receptor suggests an anion-π-type interaction may enhance nitrate binding.

Recently, examples indicating the presence of anion-π interactions in solution have emerged, often accompanied by complementary solid state evidence. A functionalized naphthalenediimide chain has shown a high selectivity for transporting nitrate over acetate in vesicles. (Dawson et al., Nat. Chem. 2010, 2, 533-538) Similarly, a perfluorobenzene calixarene-based ditopic receptor showed chloride ion transport across a lipid membrane despite a lack of detectable chloride binding via 19F NMR spectroscopy. (Jentzsch et al., Angew. Chem. Int. Ed. 2011, 50, 11675-11678) Attempts to quantify non-charge-transfer anion-π interactions have proved difficult because of their innate weakness; however, an "enforced proximity" approach has been used to quantify a small but favorable anion-π interaction in a nitrosubstituted octamethyl calix[4]pyrrole. (Gil-Ramirez et al, Angew. Che. Int. Ed. 2008, 47, 4114-4118) Most recently, nitrate-π interactions have been further quantified for a series of disubstituted calix[4]pyrroles, in which nitrate is likely sandwiched between two electron-deficient aryl substituents. (Adrianessens et al, J. Am. Chem. Soc. 2013, 135, 8324-8330) Two such receptors showed selectivity for the transport of nitrate over chloride across lipid membranes. (Adrianessens et al, J. Am. Chem. Soc. 2013, 135, 8324-8330) The work disclosed herein suggests an influence of anion-π-type interactions in the observed nitrate selectivity.

Molecular models suggested the tripodal structure and urea functionalities are likely to bind trigonal planar anions. Nitrate should be able to accommodate six hydrogen bond donors, which is more easily accomplished with diprotic donors, such as ureas. In addition, the electron-deficient central arene of the tripodal receptors would enhance the chances of a three-fold symmetric binding motif.

Disclosed herein in one embodiment is a compound, or a protonate or salt thereof, having the formula I of:

wherein Y represents an optionally substituted aromatic group;

n is 1 or 2;

a is 0 to 4;

$R^1$ and $R^2$ are each independently H; optionally substituted alkyl; optionally substituted aralkyl; acyl; phosphonyl; $-SO_2R^{12}$; $-C(O)R^{13}$; $-C(O)OR^{14}$; $-C(O)NR^{15}R^{16}$; $-C(O)CH_2R^{17}$; or $-C(S)-NR^{18}R^{19}$; $-S(O)R^{20}$; or $-SO_2NR^{21}R^{22}$, wherein $R^{12}$-$R^{22}$ are each independently H, optionally substituted alkyl, optionally substituted aralkyl, optionally substituted aryl, or $-C(O)R^{23}$, wherein $R^{23}$ is H, optionally substituted alkyl, optionally substituted aralkyl, or optionally substituted aryl; and each $R^3$ is independently optionally substituted alkyl, halogen, optionally substituted alkoxy, optionally substituted carboxyl, amide; amino; or nitro.

In certain embodiments, there is disclosed a compound, or a protonate or salt thereof, having the formula II of:

wherein n, a, Y, $R^1$, $R^2$ and $R^3$ are the same as in formula I.

In certain embodiments of formula I or II, n is 1.

In certain embodiments of formula I or II, a is 1, and the $R^3$ group is at a para position relative to the position of the $NR^1R^2$ group.

In certain embodiments of formula I or II, $NR^1R^2$ is a diprotic donor.

In certain embodiments of formula I or II, at least one of $R^1$ or $R^2$ is independently selected from:

wherein $R^4$ is H or optionally substituted alkyl;

$R^5$ is H or optionally substituted aryl;

$R^6$ is H, acyl, optionally substituted aryl, or optionally substituted alkyl;

$R^7$ and $R^8$ are each independently H or optionally substituted alkyl;

each X is independently selected from a lower alkyl, halogen, nitro, optionally substituted alkoxy, optionally substituted carboxyl, or amide;

Z is O or S; and b is 0 to 5.

In certain embodiments of formula I or II, each $R^1$ is H and each $R^2$ is independently selected from:

wherein
R[4] is H or optionally substituted alkyl;
R[5] is H or optionally substituted aryl;
R[6] is H, acyl, optionally substituted aryl, or optionally substituted alkyl;
R[7] and R[8] are each independently H, optionally substituted aryl, or optionally substituted alkyl; each X is independently selected from an optionally substituted lower alkyl, halogen, nitro, optionally substituted lower alkoxy, optionally substituted aryloxy, optionally substituted carboxyl, azide, sulfonate, sulfonic acid, or amide;
Z is O or S; and
b is 0 to 5.

In certain embodiments, R[4] is H.

In certain embodiments, R[5] is phenyl or phenyl substituted with lower alkyl, halogen, nitro, optionally substituted alkoxy, optionally substituted carboxyl, or amide.

In certain embodiments, R[6] is H, optionally substituted phenyl, or optionally substituted lower alkyl.

In certain embodiments, at least one of R[7] or R[8] is optionally substituted lower alkyl.

In certain embodiments, b is 1. In certain embodiments, b is 1 and the X group is in a para position relative to the position of the NR[4]C(O)—NH group or the NR[4]S(O)$_2$ group. The X group can be selected for several purposes. Typically, X is selected to tune or tailor the electronics of the ring by selecting an electron donating or electron withdrawing and/or conjugated group. In other examples, X is selected for detection purposes, or, for instance, to affect the solubility of the overall molecule. Suitable X groups include, without limitation those listed in Table 1.

| Substituent | Hammett constant ($\sigma_{para}$) |
|---|---|
| —H | 0.00 |
| —OCH$_3$ | −0.27 |
| —CH$_3$ | −0.04 |
| —CH$_2$CH$_3$ | −0.05 |
| —C(CH$_3$)$_3$ | |
| —F | 0.06 |
| —Cl | 0.23 |
| —Br | 0.23 |
| —I | 0.18 |
| —CF$_3$ | 0.54 |
| —OCF$_3$ | |
| —NO$_2$ | 0.78 |
|  | |
| —N$_3$ | |
| —CN | 0.66 |
| —OH | −0.37 |

| Substituent | Hammett constant ($\sigma_{para}$) |
|---|---|
| —NH$_2$ | −0.66 |
|  | −0.83 |
|  | 0.45 |
| —SO$_3^-$ | 0.09 |

In certain embodiments of formula I or II, R[3] is a lower alkyl such as methyl, ethyl, n-propyl, isopropyl, n-butyl, isobutyl, t-butyl, pentyl, or hexyl.

In certain embodiments of formula I or II, Y is an optionally substituted aryl or heteroaryl, particularly an N-heteroaryl. In certain embodiments, Y is an electron-deficient aromatic group. A particularly preferred Y is an optionally substituted phenylene. For example, Y may be wherein each of R[9], R[10] or R[11] is independently selected from H, an alkyl, or an electron withdrawing group such as, for example, halogen, nitrile or trifluoromethyl. In certain embodiments, each of R[9], R[10] and R[11] is an electron withdrawing group. In certain embodiments, each of R[9], R[10] and R[11] is halogen, particularly the same halogen such as F.

Illustrative N-heteroaryls include

, and

In certain embodiments of formulae I or II, n is 1; a is 1; R$^1$ is H; R$^2$ is

R$^3$ is lower alkyl at a para position relative to the position of the NR$^1$R$^2$ group; R$^4$ is H; X is at a para position relative to the position of the NR$^4$C(O)—NH group; and Y is wherein each of R$^9$, R$^{10}$ or R$^{11}$ is halogen or alkyl. In certain embodiments, each of R$^9$, R$^{10}$ and R$^{11}$ is halogen, particularly the same halogen such as F.

Illustrative tripodal receptor compounds include:

13
-continued

14
-continued

-continued

The compounds disclosed herein are inclusive of their protonated forms, salt forms, and N-oxide forms.

The disclosed host compounds are useful for binding and/or detecting ligands, in particular ionic ligands, including anionic ligands, and particularly oxyanions. The ligands may be inorganic or organic, but generally are inorganic. Particular examples of anionic ligands bound and/or recognized by the disclosed host compounds include, without limitation sulfate, (e.g, hydrogen sulfate), phosphate (e.g. hydrogen phosphate or dihydrogen phosphate), perchlorate, perrhenate, nitrate, chloride or bromide. Exemplary host compounds exhibit ligand binding selectivity or recognition, particularly for nitrates, for example, sodium nitrate or potassium nitrate. The host compounds may exhibit selectivity in binding of the ligand or reporting of a ligand's presence.

In certain embodiments, the presence of nitrate or any other anion of interest (including quantitative levels) can be detected in samples (e.g., a sample from a body of water such as a river, lake or pond or a soil sample) using the receptors disclosed herein. For example, the receptors may be embedded in polymers/membranes/supports for sensing and/or pre-concentration of analytes.

EXAMPLES

The 1,3,5-trifluorobenzene core (3) was obtained in 93% yield through a Sonogashira cross-coupling at 70° C. between 1,3,5-trifluoro-2,4,6-triiodobenzene (Hennrich et al., Tetrahedron Lett. 2004, 45, 1147-1149) and 4-t-butyl-2-ethynylaniline (Scheme 1). (Carroll et al., Chem. Commun. 2009, 2520-2522; Wan et al. J. Org. Chem. 2001, 66, 3893-3901). Similarly, the unsubstituted core (4) was synthesized in 60% yield from triiodobenzene. (Chaikovskii et al, Russ. J. Org. Chem. 2007, 43, 1291-1296). For comparison, an unsubstituted, more electron-rich version (2) was synthesized. Subsequent reaction of 3 and 4 with p-nitrophenylisocyanate in toluene provided receptor 1 in 67% yield and 2 in 57% yield, respectively.

Scheme 1

Figure 1:
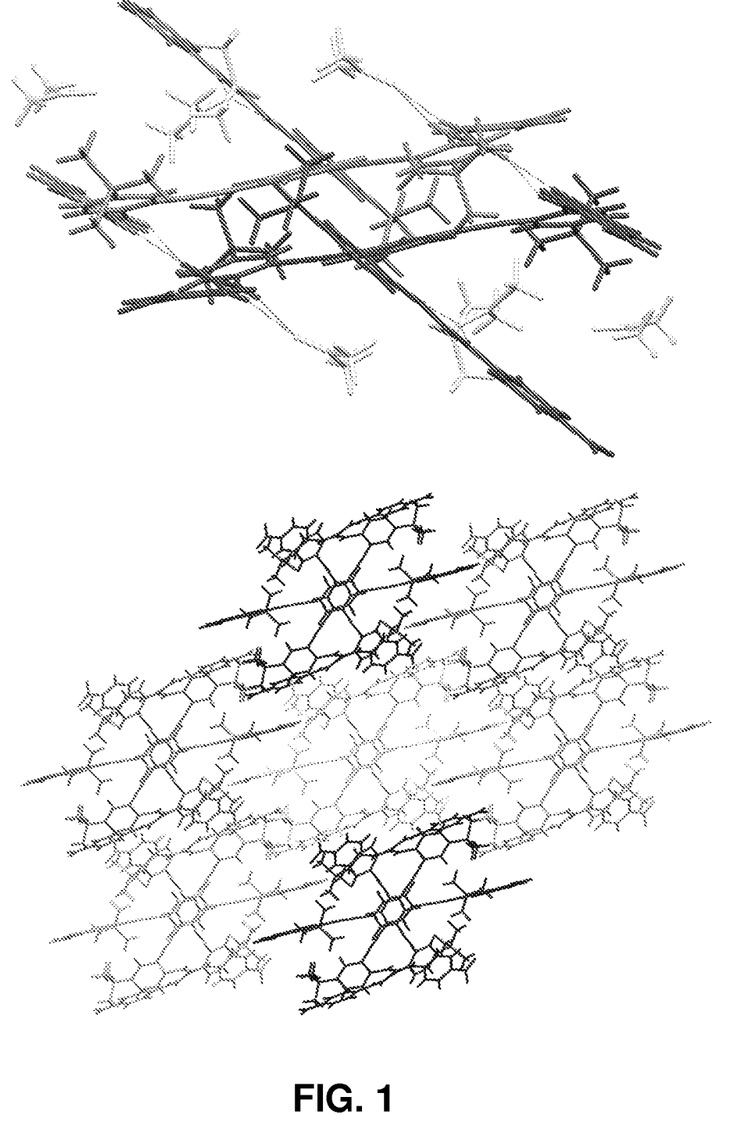
FIG. 1 shows crystal packing of compound 1 (top) showing a dimer capped by a total of eight acetone molecules and (bottom) showing these dimers are mostly discrete, interacting with each other through only π-stacking (solvent omitted for clarity).

Single crystals of 1 were obtained by vapor diffusion of pentane into acetone. The solid state structure shows a tight dimer held together by an intricate network of hydrogen bonds (FIG. 1). Two monomers stack on top of each other through slip-stacked π-π interactions of the central benzene. Two urea arms on one host molecule bind two urea arms on the second host, one as the donor, the other as the acceptor. The urea protons not involved in interactions of self-association bind acetone molecules. The third arm of each monomer sticks out of the plane defined by the core and the other two arms. The dimer is capped on each side by a total of eight acetone molecules. Each dimer interacts with another through π-stacking of the third protruding arm.

Interaction of 1 with anions in solution was investigated by 1H NMR spectroscopy. Initial titration experiments were performed at 0.5 mM of 1 in acetone-d6 due to its limited solubility in other solvents, despite the potential solvent competition as a hydrogen bond acceptor. Addition of tetrabutylammonium (TBA) salts of chloride, bromide, and nitrate resulted in a downfield shift of both urea protons, $H^a$ and $H^b$ (labels refer to assignments shown in Scheme 1). Changes in chemical shifts of $H^c$ and $H^d$ were also observed, but to a lesser extent, with $H^d$ moving upfield. Large downfield shifts of the urea protons indicate hydrogen bonds of the ureas to the anion as the main mode of binding. Change in chemical shift corresponding to the addition of $NO_3^-$ or $Br^-$ begins to maximize at approximately 0.5 equiv. of guest, indicating a possible 2:1 binding model in acetone. Linear regression analysis of these data failed to provide reproducible binding constants with 1:1 or 2:1 models for $NO_3^-$ or $Br^-$. The sharp transition seen in the binding curves often indicates strong binding with $K_a > 10^4$ $M^{-1}$ which is often too large to be accurately determined by NMR spectroscopy. Titrations with $Cl^-$ showed the Δδ maximizing closer to 1 equiv. of guest. Linear regression analysis of these data provided a 1:1 binding constant for $Cl^-$ of 8620±1170 M-1. This evidence alone is not enough to demonstrate the proposed stronger binding of $NO_3^-$ than $Cl^-$ for 1; however, it does indicate a strong binding of $NO_3^-$ in acetone and suggests a lower limit for the $NO_3^-$ association constant. For comparison, to the best of our knowledge, the largest association constants previously reported in the literature for nitrate binding of neutral receptors in acetone are 3470 $M^{-1}$ for a p-ureapyridine-based receptor and 910 $M^{-1}$ for a 1,4-diaryl triazole oligomer.

Preferential binding of chloride and nitrate to 1 over the competitive solvent acetone was also demonstrated in the solid state (FIG. 2). Single crystals of 1 binding TBACl and TBANO₃ were grown through vapor diffusion of pentane into acetone. Comparison of the solid state structures shows the packing of 1 with $NO_3$ (FIG. 2c,g) and with $Cl^-$ (FIG. 2d,h) to be remarkably similar. A single host molecule binds two anions through hydrogen bonds to the ureas of two arms (FIGS. 2a and 2b). The hydrogen bonds between 1 and $NO_3^-$ are shorter than those of 1 and $Cl^-$, with $N_{urea} \cdot O_{nitrate}$ distances of 2.874(6) and 3.089(6) Å for one urea and 3.008(5) and 2.887(5) Å for the other, compared to $N_{urea} \cdot Cl^-$ distances of 3.324(3) and 3.244(3) Å for one urea and 3.175(3) and 3.314(3) Å for the other. Each anion is located over the alkyne of a single monomer. Once again, $NO_3^-$ is held closer to the monomer than $Cl^-$, as seen in FIGS. 2e and 2f. The closest interaction of $Cl^-$ to the monomer is to one alkyne carbon with a distance of 3.796 Å. However, for nitrate the anionic π-system appears to align with the π-system of the receptor, supporting some intermolecular distances <3.7 Å (FIG. 2f). Crystal packing shows an overall 1:1 binding where the host and anion are arranged in an infinite chain of host:guest:host:guest, etc. (FIG. 2c). As mentioned, the anion is bound to the host through hydrogen bonds to both urea hydrogens on a single arm of the structure. The urea carbonyl of the same arm is hydrogen bonded to an arm on the receptor, which shares binding to the anion. TBA countercations form solvent-separated ion pairs with both $NO_3^-$ (FIG. 2g) and $Cl^-$ FIG. 2h) and are in approximately the same location in each crystal structure.

Figure 3:
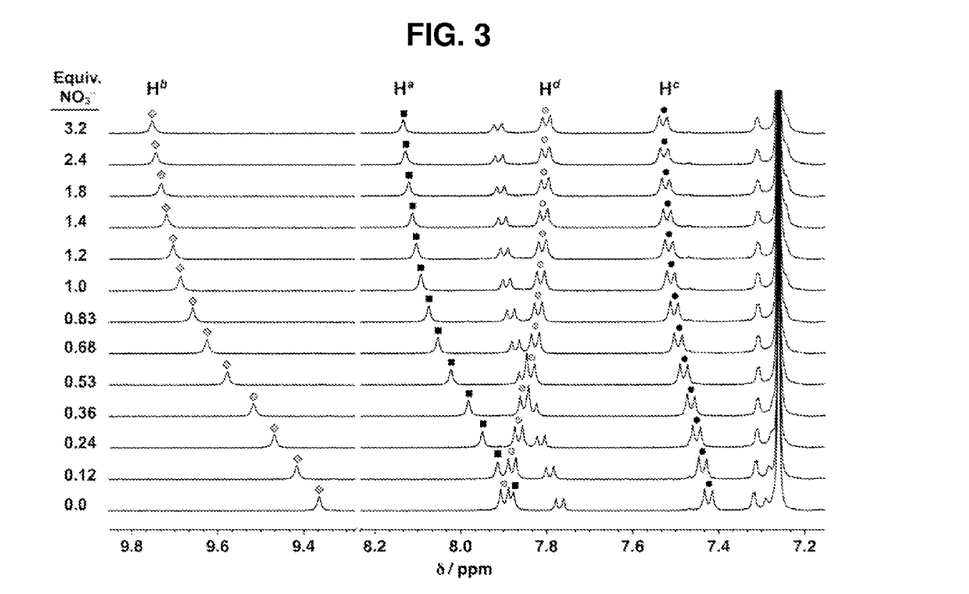
FIG. 3 is a graph showing an example stacked $^1$H NMR spectra for the titration of nitrate into a 1 mM solution of receptor 1 in 10% DMSO-d$_6$/CDCl$_3$.

To simplify the mode of binding in these receptors, as well as to lower the association constant of nitrate and bromide to a measurable amount, other solvent systems were investigated. Low solubility of the tripodal receptors limited the solvent possibilities. We also aimed to maintain competition between binding of the anion and solvent molecules to provide further evidence for the strong binding of nitrate in competitive solvents, a critical feature for applications in environmental monitoring. Increasing concentrations of DMSO in chloroform have been shown to simplify binding models by breaking up self-association and, as a result, higher order binding. In addition, DMSO is a strong hydrogen bond acceptor, thus a lower association constant would be expected. Initial upfield shifts, followed by downfield shifts of the urea protons were observed upon the addition of TBANO₃ 1 mM solutions of 1 in 2% DMSO-d₆/CDCl₃ and 5% DMSO-d₆/CDCl₃. The titration curves indicate a more complicated system than a 1:1 model; however, the data still could not be fit to a standard model. Raising the DMSO concentration to 10% DMSO-d6/CDCl₃ decreased the overall change in chemical shift of the urea protons (FIG. 3), but a smooth binding curve is observed, indicating self-aggregation (and likely ion-pairing) is no longer occurring. As suspected, titrations of TBA salts of nitrate, bromide, chloride, and iodide fit to a 1:1 model when performed in 10% DMSO-d6/CDCl₃ (Table 1).

Titrations in 10% DMSO-d6/CDCl₃ were performed at a constant 1 mM concentration of 1. The change in chemical shift was monitored throughout the titration and fit to a 1:1 model using linear regression analysis. Titrations of $NO_3^-$, $Cl^-$, and $Br^-$ performed with 1 showed Δδ level off at approximately 1 equiv. of guest, while $I^-$ began to maximize closer to 3 equiv. The binding constants of each anion investigated and the calculated total Δδ values based on the determined constant are presented in Table 2. The largest changes in chemical shift for each anion are observed in the urea protons of 1, $H^a$ and $H^b$. $H^b$ moves farthest downfield, demonstrating a stronger hydrogen bond between the anion and this proton. Chloride has the largest shift in $H^b$ but its measured $K_a$ of 12,200 M-1 was not the highest observed association with 1.

TABLE 2

Association constants ($K_a$, M$^{-1}$) of compounds 1 and 2 with tetrabutylammonium anions in 10% DMSO-d$_6$/CDCl$_3$ determined by monitoring the urea protons, H$^a$ and H$^b$, during $^1$H NMR titrations.

| | 1 | | | | | 2 |
|---|---|---|---|---|---|---|
| Anion[ii] | Δδ(H$^a$)[iii] (ppm) | Δδ(H$^b$)[iii] (ppm) | Δδ(H$^c$)[iii] (ppm) | Δδ(H$^d$)[iii] (ppm) | $K_a$[iv] (M$^{-1}$) | Δδ(H$^a$)[iii] (ppm) |
| NO$_3^-$ | 0.26 | 0.39 | 0.10 | −0.10 | 24100 (1050) | 0.19 |
| Cl$^-$ | 0.21 | 0.99 | 0.17 | −0.15 | 12200 (934) | 0.12 |
| Br$^-$ | 0.16 | 0.62 | 0.17 | −0.11 | 8320 (876) | |
| I$^-$[vi] | 0.12 | 0.29 | 0.16 | −0.07 | 755 (85) | |

| | 2 | | | | |
|---|---|---|---|---|---|
| Anion[ii] | Δδ(H$^b$)[iii] (ppm) | Δδ(H$^c$)[iii] (ppm) | Δδ(H$^d$)[iii] (ppm) | Δδ(H$^{core}$)[v] (ppm) | $K_a$[iv] (M$^{-1}$) |
| NO$_3^-$ | 0.27 | 0.12 | −0.06 | <0.01 | 11800 (1570) |
| Cl$^-$ | 0.97 | 0.21 | −0.07 | 0.31 | 63700 (814) |
| Br$^-$ | | | | | __[vii] |
| I$^-$[vi] | | | | | __[vii] |

The largest association constant of 24,100 M$^{-1}$ was obtained with NO$_3^-$, which also had the largest observed shift in H$^a$, 0.26 ppm versus 0.21, 0.16, and 0.12 ppm for Cl$^-$, Br$^-$, and I$^-$, respectively. Comparing the other values of H$^a$ with the binding constants, a trend is observed: the larger shift in H$^a$, the higher the measured 1:1 association constant. Not only is 1 capable of binding anions out of competitive media, the binding of nitrate is significantly higher than chloride. The only comparison in 10% DMSO-d6/CDCl$_3$ these inventors are aware of is a neutral tripodal cyclic peptide with a 1:1 NO$_3^-$ binding constant of 126 M$^{-1}$ and no selectivity for NO$_3$ is observed. Selectivity for NO$_3^-$ over Cl$^-$ and I$^-$ has been demonstrated in 100% DMSO-d6 for a NHBoc-substituted macrocyclic triamide with a NO$_3^-$ association constant of 20 M$^{-1}$. To the best of our knowledge, tripodal host 1 exhibits the strongest nitrate binding for a neutral receptor in competitive solvents, and an anion-π interaction appears to facilitate, if not enhance, this binding.

Figure 2A:
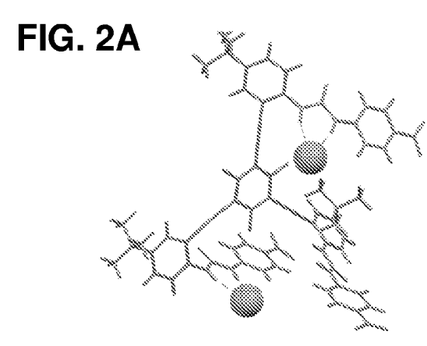
FIG. 2 shows crystal packing of compound 1 with (a,c,e,g) TBACl and (b,d,f,h) TBANO$_3$, highlighting the overall 1:1 interactions between host and anionic guest in the (a,b) monomer, (c,d) stacked column, and with the conjugated π-system (e,f). Cation (blue) and solvent (orange) interactions are shown in g and h.
Figure 2B:
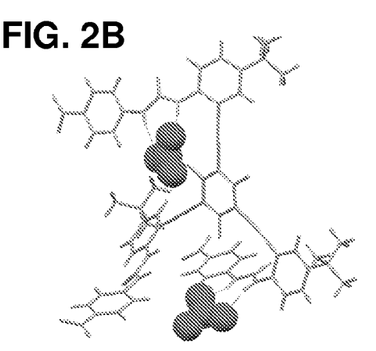
Figure 2C:
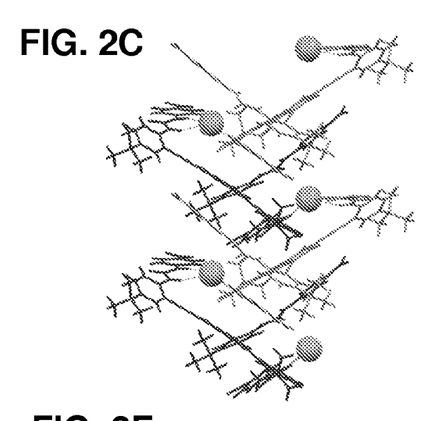
Figure 2D:
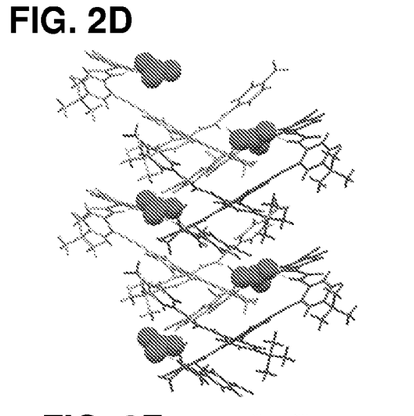
Figure 2E:
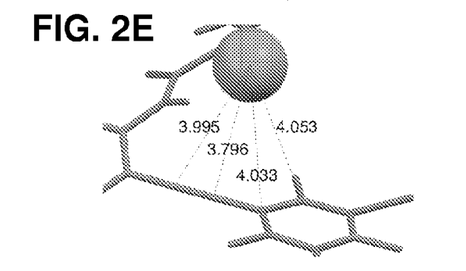
Figure 2F:
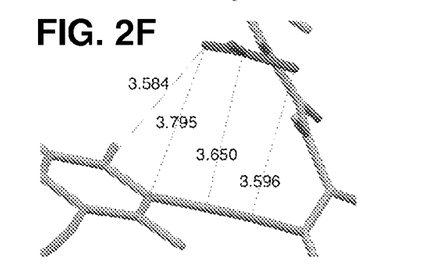
Figure 2G:
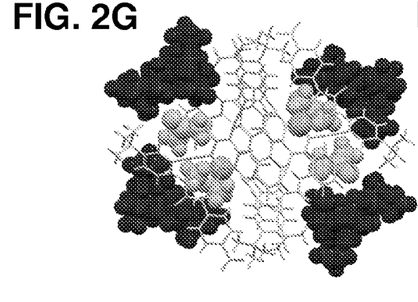
Figure 2H:
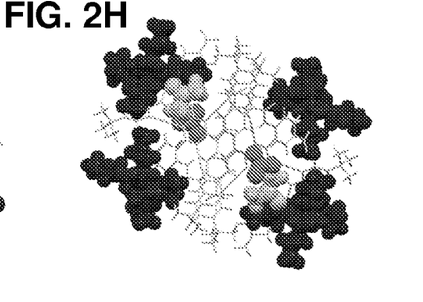

The trend in binding constants corresponds to the observed Δδ values of H$^a$. A larger value of Δδ would typically indicate a stronger and shorter hydrogen bond of the urea proton to the anion, which would correspond to the anion being in closer proximity to the aryl core. This presents an argument for the presence of an anion-π interaction. The crystal structure of the nitrate-bound host supports this hypothesis, and reveals a clear interaction between the nitrate anion and the π-system of the aryl core and the alkyne (for example, see FIG. 2f showing N/O$_{nitrate}$·C$_{alkynyl}$ contacts distances of 3.596 and 3.650 Å). As previously discussed, the distances of NO$_3^-$ to the aryl core and alkyne are significantly shorter than those of Cl$^-$. An electrostatic potential map of 1 indicates a lack of electron density in the arene as well as the conjugated alkynes. The question arises as to why nitrate would have a stronger interaction with the π-system than chloride. Nitrate itself possesses a conjugated π-system, so this could be suggestive of a favorable π-π type interaction; nevertheless, one of the partners in this interaction is anionic making this a clear example of an anion-π interaction of some type or a "π-π-assisted anion-π" interaction.

To further investigate this claim, unsubstituted and more electron-rich receptor 2 was synthesized for comparison to electron-deficient 1. In addition to the change in electronics providing weakened anion-π interactions, the extra proton in 2, H$^{core}$, could provide further insight into the binding mode.

Figure 4A:
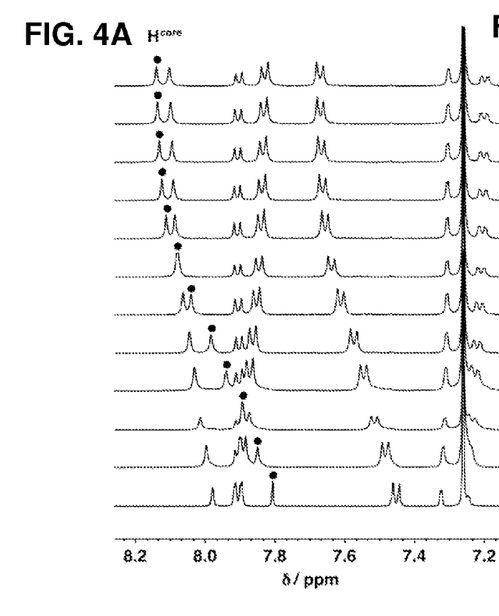
FIG. 4 is a graph showing a stacked $^1$H NMR spectra for the titration of (a) Cl$^-$ and (b) NO$_3^-$ into a 1 mM solution of receptor 1 in 10% DMSO-d$_6$/CDCl$_3$.
Figure 4B:
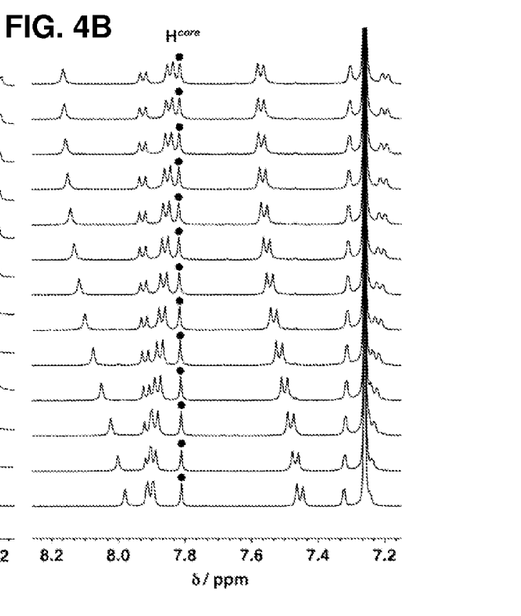

Similar to 1, host:guest complexes of 2 were investigated through 1H NMR spectroscopy titrations in 10% DMSO-d6/CDCl$_3$. Titrations were performed at approximately 1 mM 2 with TBA salts of Cl$^-$ and NO$_3^-$. The urea protons (H$^a$ and H$^b$), nitrophenyl protons (H$^c$ and H$^d$), and core proton (H$^{core}$) were monitored throughout the titrations. For consistency, only H$^a$, H$^b$, H$^c$, and H$^d$ were used to fit the data to a 1:1 model, as was done with 1. All changes in chemical shift began to level off near 1 equiv. of anion and are presented in Table 1 with the association constants corresponding to NO$_3^-$ and Cl$^-$. The values reported for H$^a$, H$^b$, H$^c$, and H$^d$ are averages derived from the individual association constants of each titration, while the values for H$^{core}$ are averaged from the observed changes during the titration. Replacing the fluorine atoms with hydrogens changes not only the electronics, but also the number of hydrogen bond donors. This combination leads to a loss in selectivity for NO$_3^-$ over Cl$^-$. Chloride binding is now enhanced, with an association constant for 2 of 63,700 M$^{-1}$ whereas nitrate binding is weakened to 11,800 M$^{-1}$. Any anion-π interactions would be weakened or now repulsive due to the change in electronics within the central ring, so weakening of the binding would be expected, as seen with NO$_3^-$. The large increase in $K_a$ for Cl$^-$ can be attributed to the addition of a hydrogen bond with H$^{core}$, assigned from the titration of 2 (FIG. 4a). This hydrogen bond is observably stronger (Δδ=0.31 ppm versus 0.12 ppm) than that of H$^a$, which correlated to $K_a$ for 1. The association constant for NO$_3^-$ with 2 trends with the noted correlation and indicates 2 may bind NO$_3^-$ by a similar mode as 1, but binds Cl$^-$ through a different mode. More importantly, no significant shift of H$^{core}$ occurs upon the addition of nitrate to 2 (FIG. 4b), thus there is no hydrogen bonding of the anion to H$^{core}$, indicating an anion-π interaction may still be the preferred mode of binding in spite of the more electron-rich arene. Three important results stem from the investigation of 2: nitrate selectivity is lost, the association constant of nitrate is diminished, and nitrate binds via a different mode than chloride. These data support a model in which nitrate binds to the receptor through an anion-π-type interaction regardless of the electronics, while chloride prefers to bind through a hydrogen bond to the core of 2 rather than to the π-system, effectively raising the association constant.

The tripodal receptors presented here demonstrate preferential binding of anions over competitive hydrogen bonding solvents, acetone-$d_6$ and 10% DMSO-$d_6$/CDCl$_3$. The binding of nitrate and bromide to 1 in acetone-d6 could not be accurately determined. The association of chloride to 1 is actually higher in the 10% DMSOd$_6$/CDCl$_3$ solution than in acetone-d6, whereas the association of both bromide and nitrate are lower. Receptors 1 and 2 bind anions out of 10% DMSO-$d_6$/CDCl$_3$ in a 1:1 stoichiometry. A strong affinity for the anions is observed even in the presence of DMSO-d6 and the binding of 1 trends: $NO_3^- > Cl^- > Br^- > I^-$, with a moderate selectivity for nitrate possibly resulting from an anion-π interaction. Binding studies of 2 support the existence of a favorable anion-π interaction by demonstrating a loss in nitrate selectivity and indicating an anion-π-type interaction to still be the preferred mode of binding for nitrate.

In view of the many possible embodiments to which the principles of the disclosed compounds and methods may be applied, it should be recognized that the illustrated embodiments are only preferred examples of the invention and should not be taken as limiting the scope of the invention.

What is claimed is:

1. A compound, or a protonate or salt thereof, having a formula I of:

wherein Y represents an optionally substituted aromatic group;
n is 1 or 2;
a is 1 to 4;
$R^1$ and $R^2$ are each independently H; optionally substituted alkyl; optionally substituted aralkyl; acyl; phosphonyl; —$SO_2R^{12}$; —$C(O)R^{13}$; —$C(O)OR^{14}$; —$C(O)NR^{15}R^{16}$; —$C(O)CH_2R^{17}$; or —$C(S)$—$NR^{18}R^{19}$; —$S(O)R^{20}$; or —$SO_2NR^{21}R^{22}$, wherein $R^{12}$-$R^{22}$ are each independently H, optionally substituted alkyl, optionally substituted aralkyl, optionally substituted aryl, or —$C(O)R^{23}$, wherein $R^{23}$ is H, optionally substituted alkyl, optionally substituted aralkyl, or optionally substituted aryl; and
at least one $R^3$ is a tert-butyl group.

2. The compound of claim 1, having a formula II of:

3. The compound of claim 1, wherein n is 1.
4. The compound of claim 1, wherein a is 1, and the $R^3$ group is at a para position relative to the position of the $NR^1R^2$ group.
5. The compound of claim 1, wherein $NR^1R^2$ is a diprotic donor.
6. The compound of claim 1, wherein $NR^1R^2$ is selected from:

wherein
$R^4$ is H or optionally substituted alkyl;
$R^5$ is H or optionally substituted aryl;
$R^6$ is H, acyl, optionally substituted aryl, or optionally substituted alkyl;
$R^7$ and $R^8$ are each independently H or optionally substituted alkyl;
each X is independently selected from a lower alkyl, halogen, nitro, optionally substituted alkoxy, optionally substituted carboxyl, or amide;
Z is O or S; and
b is 0 to 5.

7. The compound of claim 1, wherein $NR^1R^2$ is selected from:

wherein
- $R^4$ is H;
- $R^5$ is H or optionally substituted aryl;
- $R^6$ is H, acyl, optionally substituted aryl, or optionally substituted alkyl;
- $R^7$ and $R^8$ are each independently H, optionally substituted aryl, or optionally substituted alkyl;
- each X is independently selected from an optionally substituted lower alkyl, halogen, nitro, optionally substituted lower alkoxy, optionally substituted carboxyl, or amide;
- Z is O or S; and
- b is 0 to 5.

8. The compound of claim 6, wherein at least one of $R^7$ or $R^8$ is a lower alkyl.

9. The compound of claim 6, wherein X is halogen or nitro.

10. The compound of claim 6, wherein b is 1 and the X group is in a para position relative to the position of the $NR^4C(O)$—NH group or the $NR^4S(O)_2$ group.

11. The compound of claim 1, wherein at least a second $R^3$ is a lower alkyl such as methyl, ethyl, n-propyl, isopropyl, n-butyl, isobutyl, t-butyl, pentyl, or hexyl.

12. The compound of claim 1, wherein Y is an optionally substituted aryl or heteroaryl.

13. The compound of claim 1, wherein Y is an electron-deficient aromatic group.

14. The compound of claim 1, wherein Y is an optionally substituted phenylene.

15. The compound of claim 1, wherein Y is wherein each of $R^9$, $R^{10}$ or $R^{11}$ is independently selected from H, alkyl, or an electron withdrawing group.

16. The compound of claim 15, wherein each of $R^9$, $R^{10}$ and $R^{11}$ is halogen or alkyl.

* * * * *